US006524343B2

(12) United States Patent
Storer et al.

(10) Patent No.: US 6,524,343 B2
(45) Date of Patent: Feb. 25, 2003

(54) FEMORAL HIP PROSTHESIS

(75) Inventors: John Andrew Storer, Bayeux (FR); Richard Eddy Field, Walton-on-the-Hill (GB); Neil Rushton, Cambridge (GB)

(73) Assignee: Benoist Girard SAS (FR)

( * ) Notice: Subject to any disclaimer, the term of this patent is extended or adjusted under 35 U.S.C. 154(b) by 0 days.

(21) Appl. No.: 09/815,867

(22) Filed: Mar. 23, 2001

(65) Prior Publication Data

US 2002/0065562 A1 May 30, 2002

(30) Foreign Application Priority Data

Mar. 27, 2000 (GB) ................................ 0007391

(51) Int. Cl.⁷ .................................. A61F 2/32
(52) U.S. Cl. ................... 623/22.46; 623/22.11
(58) Field of Search .................. 623/22.46, 22.3, 623/22.21, 22.38, 22.35, 22.11, 23.11, 23.14, 23.18, 908, 22.41, 22.43, 22.45; 606/89, 63, 67

(56) References Cited

U.S. PATENT DOCUMENTS

| 4,385,405 A | * | 5/1983 | Teinturier |
| 4,608,055 A | * | 8/1986 | Morrey et al. |
| 4,752,296 A | * | 6/1988 | Buechel et al. |
| 5,571,203 A | * | 11/1996 | Masini |
| 6,096,084 A | | 8/2000 | Townley |

FOREIGN PATENT DOCUMENTS

| DE | 923383 | 8/1951 |
| DE | 3840471 | 9/1990 |
| FR | 995762 | 12/1951 |
| FR | 1017927 | 12/1952 |
| FR | 1 107 877 | 1/1956 |
| FR | 2578739 | 9/1986 |
| FR | 299 400 | 6/1994 |
| GB | 719 308 | 12/1954 |
| GB | 2139097 | 11/1984 |
| WO | WO 98/07393 | 2/1998 |
| WO | WO 00/45750 | 10/2000 |

* cited by examiner

Primary Examiner—Pedro Philogene
(74) Attorney, Agent, or Firm—Lerner, David, Littenberg, Krumholz & Mentlik, LLP

(57) ABSTRACT

A prosthetic femoral component is located in a prepared socket in a femur which has been resected at a position on the proximal side of its neck and Includes a tapered insert and a proximal head portion. The proximal end of the insert portion is adapted for location in the prepared socket and has a maximum dimension in a plane normal to the distal-proximal axis of the neck which is larger than the minimum dimension of the neck in a parallel plane. The component takes advantage of the bone at the periphery of the socket which enables the insert to be accurately and firmly located in the bone. The presence of the bone at the outer edges of the socket helps to stabilize the component. Preferably the tapered insert portion is flared outwardly in the proximal direction. The tapered insert portion can be dimensioned to pass through the neck of the femur with which it is to be used or it can stop short of it.

51 Claims, 3 Drawing Sheets

FEMORAL HIP PROSTHESIS

BACKGROUND OF THE INVENTION

This invention relates to a prosthetic femoral component of the type which is applied without a stem in the medullary canal, which is considered to be conservative and bone sparing.

For present purposes the definition of a conservative femoral hip prosthesis is a prosthesis which leaves sufficient bone in place for it to be eventually replaced by a more conventional femoral hip prosthesis with a medullary stem normally intended for primary (non-revision) application. A bone-sparing femoral hip prosthesis is one which limits the removal of viable bone by conserving some of the femoral head, removing only sufficient bone to resect the diseased tissue and to effect a satisfactory anchorage.

The use of a femoral hip prosthesis which functions without a stem in the medullary canal date from the first total hip prosthesis reported by Wyles in 1937. This hip prosthesis was fitted following a high resection of the femoral head and was stabilized with a straight stem which passed along the femoral neck and out below the greater trochanter, where it was attached to a bone plate secured on the lateral cortex of the femur. The Wyles hip restored the femoral head with a bearing diameter deliberately smaller than the natural femoral head it was replacing. Only six cases were ever performed using this device since the clinical outcome was not impressive.

Another femoral hip prosthesis design following that of Wyles was the Judet prosthesis, developed in France and used in the period 1945–55. A high neck resection was used with this prosthesis, which attempted to restore the femoral head to its natural diameter for use as a hemiarthroplasty. The prosthesis comprised an acrylic (low modulus) head and a short straight stem which passed along the femoral neck. The prosthetic head included a trough around the stem attachment to the head, which was used to seat and locate the prosthesis on the prepared proximal end of the femoral neck. Early breakage caused the stem to be given a stainless steel core support. Later failures saw the device breaking out through the inferior femoral neck. All versions of this prosthesis suffered from premature wear of the acrylic head.

High neck resections, i.e. those conserving the femoral neck, were also used by femoral hip prostheses with stems passing into the medullary canal, notably the designs of Pipino (1978) and Freeman (1985). These hip prostheses were implanted both cement-free and with cement, but did not attempt to restore the femoral head to its natural diameter, being used as total hip replacements with a head of smaller dimensions. Since these femoral hip replacements do place a stem in the medullary canal, they are not considered to be conservative, although the stem on the Pipino design was very short.

Designs of the femoral hip prostheses which have attempted to secure the replacement of the femoral head without a stem in the medullary canal follow the design of Vincent and Munting reported in 1982, which is still in clinical use. With this design, a portion of the femoral neck is preserved and shaped with a notch to provide seating for the implant. The prosthesis is used as a total hip replacement and replaces part of the femoral neck and the femoral head with a head of smaller diameter than the natural head. The prosthesis is used uncemented and is fixed with a large screw through the lateral cortex into the body of the prosthesis. The prosthesis is intended to sit on the remaining cortex of the neck and is stabilized by fins parallel to the axis of the neck which pass into the remaining diaphyseal cancellous bone. The bone engaging surfaces are provided with a hydroxyapatite coating to promote bone ongrowth to augment fixation.

The Vincent-Munting prosthesis is considered to be conservative but not bone sparing, according to the definitions given above. The only type of femoral hip prosthesis which has been developed which is conservative and bone sparing is the femoral cap used in prostheses such as the ICLH (Freeman, 1973), the THARIES (Amstutz, 1976), the Wagner (Wagner, 1973), the Zephyr (Aubriot, 1977) and the Gerard (Gerard, 1975). This type of prosthesis comprised a metal cap with a part-spherical external form and different internal forms and was used both cemented and uncemented. The bearing surface of the femoral cap was always near to anatomical size, therefore the cap could be used as a hemiarthroplasty. Mechanical loosening through stress concentration at the bone interface were reported as well as resorption of epiphyseal bone beneath the cap. The cause of the bone resorption was associated with disruption of the blood supply to regions of bone as a result of the surgical technique. Often the cap was used to articulate with a polyethylene liner in the acetabulum, and with this an additional failure mode of osteolysis at the bone interface with the prosthesis was caused by the ingress of polyethylene debris.

A development of the femoral cap design was the inclusion of a short stem to the cap. Examples of such designs include the TARA hip (1970's) and, more recently the McMinn hip (1990's).

An alternative design approach for the femoral cup is presented in U.S. Pat. Nos. 4,532,660 and 4,662,888, which describe a stemless femoral hip prosthesis intended to load the bone naturally. The first design required the resection of most the femoral head and part of the neck, the later design required only the resection of the proximal portion of the femoral head up to the epiphyseal scar plate. In the later design, a low modulus material between the bone and the femoral cap was used to transfer load with a more physiological force distribution onto the trabecular structure of the proximal femur. In practice, too little bone was removed for adequate surgical exposure of the acetabulum without excessive soft tissue damage. Furthermore, controlled exposure of the three-dimensional epiphyseal scar plate proved to be too complex and the design was never developed into an implant.

Cemented intramedullary fixation of femoral hip prostheses has now approximately 30 years successful clinical results and is the benchmark against which new designs of hip implants are assessed. Early problems of implant fracture, corrosion, cement mantle integrity and excessive bearing wear have now been largely resolved and the main problem which limits the life expectancy of conventional femoral hip prostheses is aseptic loosening. Nevertheless, since premature failure of the reconstruction may occur due to loosening, eventual revision of the prosthesis, particularly when used for younger patients (under 65), must be considered.

The revision of cemented stemmed femoral hip prostheses is challenging, particularly as a result of needing to remove all the cement. In fact, cementless stems with intramedullary fixation have been developed to simplify the revision procedure. Such devices require increased surgical precision compared with cemented hip prostheses and have their own failure modes such as pain, loosening and subsidence.

It is the likelihood of subsequent revision for the younger and more active patient which makes a conservative, and indeed bone sparing, femoral hip prosthesis an attractive option. In theory, such a device may be revised with a conventional primary stemmed hip prosthesis without the need for bone grafting or other augmentation. Indeed, there is no reason why conservative hip designs could not be at least as safe and efficacious as intramedullary stemmed hip designs. However, attempts so far to develop a conservative, bone sparing femoral hip prosthesis have encountered significantly worse results due to premature loosening of the femoral component (and acetabular component).

The present design seeks to provide a conservative, bone sparing femoral hip prosthesis that addresses the problems encountered by previous designs. The prosthesis includes an insert portion which is designed to control the ,transfer of load to the femur so as to avoid stress concentration at the bone interface. The insert portion is sized so that it replaces all the epiphyseal bone thereby minimizing the risk of bone resorption due to disrupted blood supply. It is also tapered so as to self seal under load so as to restrict the ingress of debris leading to osteolysis.

In addition to addressing the deficiencies of previous designs, the present design seeks to simplify the surgical technique so as to achieve better reproductability of results to minimize the trauma (e.g. loss of blood, post-operative infection) associated with the procedure.

Hip replacement is usually performed with a large exposure. Early post-operative infection is no longer a significant problem, but the time to heal such a major wound is significant. Some surgeons now implant conventional stemmed devices with as small an incision as they possibly can. After the femoral head and neck have been removed, only narrow tools are needed to prepare the femoral canal and there is easy access to the acetabulum. However, the bone sparing femoral hip prosthesis designs generally necessitate reverting to a wider exposure for two reasons. Firstly, the preparation of the outside of the femoral head involves bulkier instruments. Secondly, the femoral head obstructs access to the acetabulum. More cutting of soft tissues attaching the femur to the pelvis is needed to maneuver the femoral head out of the way.

SUMMARY OF THE INVENTION

The present invention is intended to provide a femoral hip prosthesis which can be employed in a method of fitting which includes cutting away the natural femoral head to expose the circular cross-section of the neck at the base of or at a mid point of the head. This allows much improved access to the acetabulum, thereby reducing the length of the required incision and minimizing the soft tissue dissection necessary to allow the remaining femoral head to be levered out of the way. The shape of the insert portion of the prosthesis is designed so as to allow it to be fitted to the bone accurately following a simple, non-bulky, reproducible reaming operation. As such, the close fit will resist micromotion and act in support of the self-sealing taper design to impede the ingress of debris. The fact that non-bulky instruments may be used allows a less-invasive surgical technique to be employed.

According to the present invention a prosthetic femoral component for location in a prepared socket in a femur which has been resected at a position on the proximal side of its neck includes a tapered insert portion and a proximal head portion, the proximal end of the insert portion being adapted for location in the prepared socket and having a maximum dimension in a plane normal to the distal-proximal axis of the neck which is larger than the minimum dimension of the neck in a parallel plane.

Thus, the component according to the present invention takes advantage of the bone at the periphery of the socket which enables the insert to be accurately and firmly located in the bone. The presence of the bone at the outer edges of the socket helps to stabilize the component. Preferably the tapered insert portion is flared outwardly in the proximal direction. The tapered insert portion can be dimensioned to pass through the neck of the femur with which it is to be used or it can stop short of it depending upon the requirements.

In one preferred embodiment the tapered insert portion has a smooth finish. This can enable it to sink into the bone if it is inserted with the use of cement. A void centering arrangement can be provided in the manner shown in U.S. Pat. No. 5,092,892.

In any case, the proximal end of the head portion can be of generally spherical shape and have a bearing surface for co-operation with an acetabular socket. The proximal end of the head portion can be provided with a male taper to receive a matching female taper on the part-spherical bearing element.

The bearing element can have a spigot adapted to engage in a bore provided in the head portion of the spigot and bore can be tapered to provide an engaging fit. In one preferred embodiment the spigot is elongated and extends through the head portion and into the tapered insert portion.

Alternatively the proximal end of the head portion can be substantially hemispherical as is the inner wall 26 of the bearing element which has a tapered elongate spigot adapted to engage in a tapered bore in a head portion to provide an engaging fit and the spigot can extend through the head portion and into the tapered insert portion to provide stability.

In any of the preceding constructions any of the parts can be made of metal, of a synthetic plastics material or a ceramic material.

In the alternative construction the prosthetic femoral component can be formed as a single component.

Preferably the tapered insert portion has a general axis which is inclined to the central axis of the head portion in a plane radial thereto.

The tapered insert portion can be non-circular and be adapted to prevent rotation relative to the bone.

Thus, the cross-section of the tapered insert portion can be elongate in a plane extending normal to the central axis. With this type of construction the cross-section of the tapered insert portion can be substantially rectangular, oval or figure-of-eight shaped or any other desired cross-section.

The tapered insert portion can be arranged to extend radially away from the distal rim of a head portion towards the central axis.

In another preferred arrangement the distal side of the head portion is formed as a trough which extend around part of the tapered insert portion and the distal portion of the insert portion can be formed with a concave taper.

If desired the proximal end of the tapered insert portion can be provided with a series of radially outward extending steps or fins.

BRIEF DESCRIPTION OF THE DRAWINGS

The invention can be performed in various ways but one embodiment will now be described by way of example and with reference to the accompanying drawings in which.

DETAILED DESCRIPTION OF THE PREFERRED EMBODIMENTS

Figure 1:
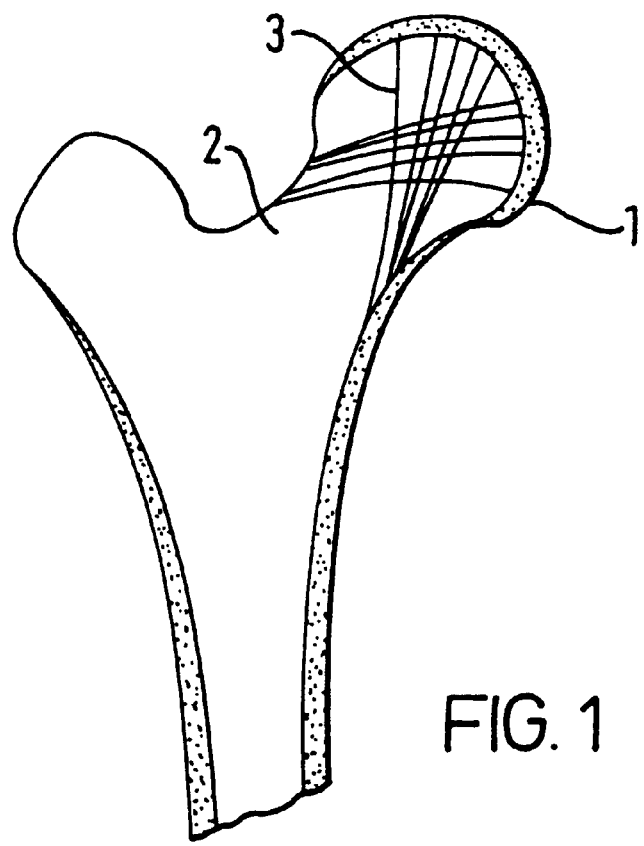
FIG. 1 is a diagrammatic view of the proximal end of a femur showing the general construction of the bone and the trabecular fibers.

As shown in FIG. 1 the natural construction of a femur consists of an outer hard bone, usually referred to as the cortex, which in the region of the ends of the femur encases a spongy interior. The cortex extends over the head of the femur, indicated by reference numeral 1, but is very thin at the junction of the head 1 and the neck 2. Trabecular fibers, indicated by reference numeral 3, sprout from the cortex upwardly and through the head 1, as shown in FIG. 1. It has been observed that, if the bone is cut, that these fibers are best able to reform around sharp surfaces.

Figure 5:
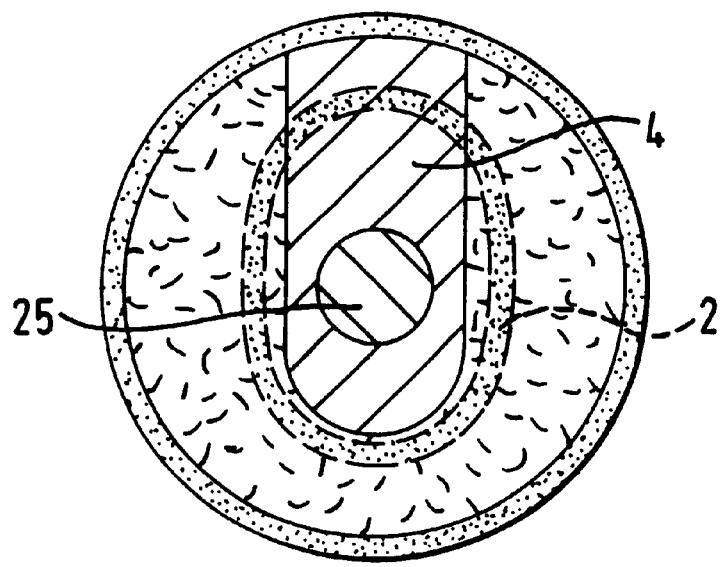
FIG. 5 is a cross-sectional view on the line V—V of FIG. 4.
Figure 6:
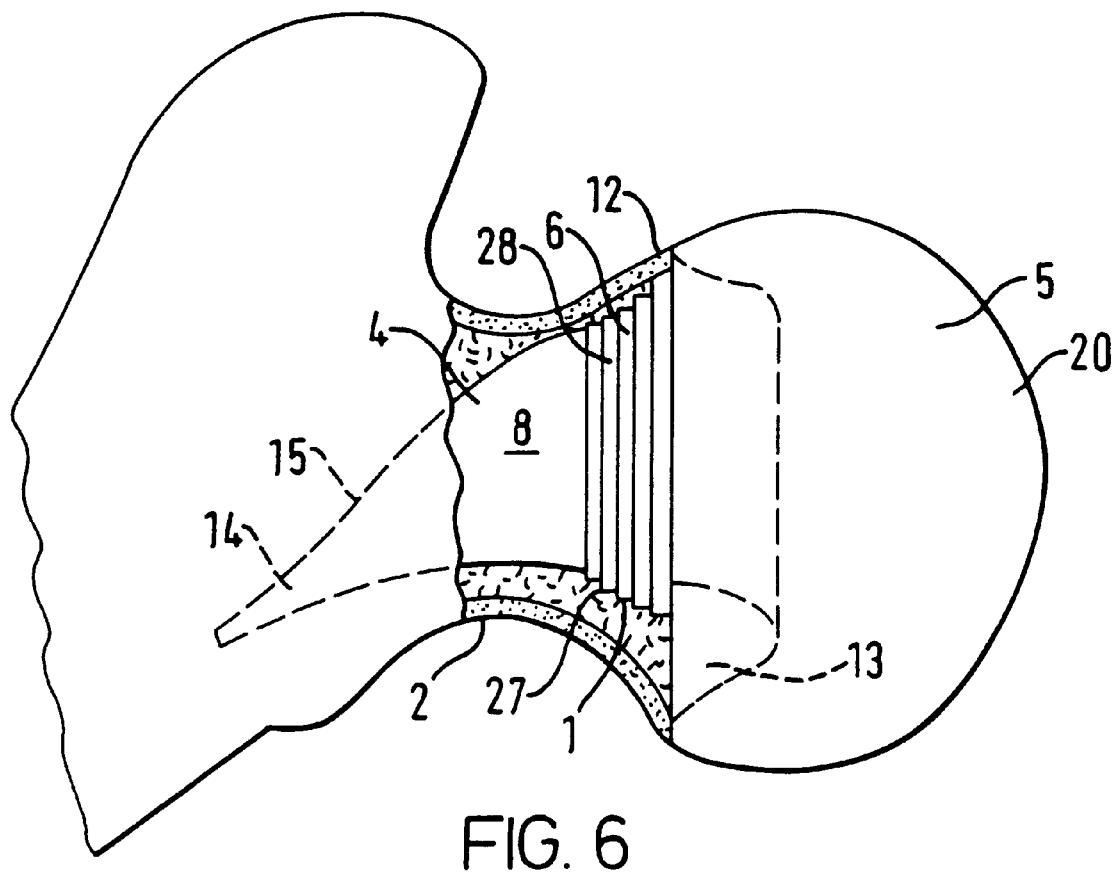
FIG. 6 is a side view of an alternative construction in place with part of the bone removed.

As shown in the drawings the prosthetic femoral component is for location in a prepared socket in a femur which has been resectioned at a position on the proximal side of its neck 2 and which includes a tapered insert portion 4 and a proximal head portion 5. The tapered insert portion 4 has a proximal end 6 which is adapted for location in the prepared socket or cavity 7 and which is flared outwardly, as indicated by reference numeral 8. The socket or cavity has a maximum dimension in a plane normal to the distal-proximal axis 9 of the neck 2 which is larger than the minimum dimension of the neck 2 in a parallel plane. This will be seen most clearly from. FIG. 5. The preferred flared bone portion extends around the anterior, posterior and medial sides of the resected head.

Figure 4:
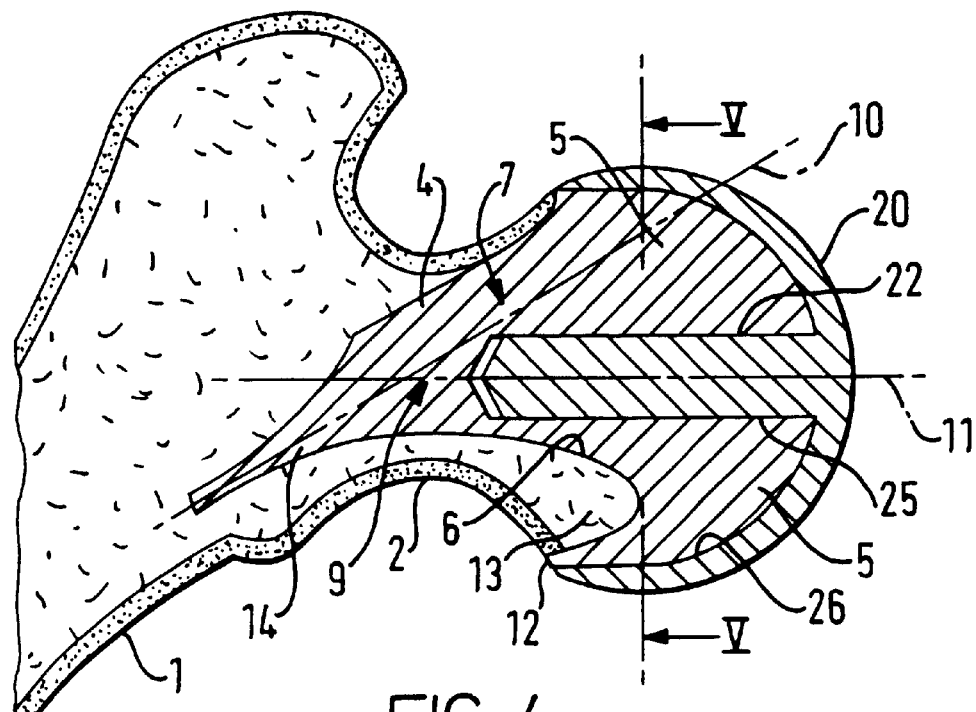
FIG. 4 is a cross-sectional side elevation of a similar construction to that shown in FIG. 3 in place in a bone.

From FIG. 4 it will also be seen that the femoral head has been transected at a point on the proximal side of the neck 2 and about half way through the femoral head.

Figure 3:
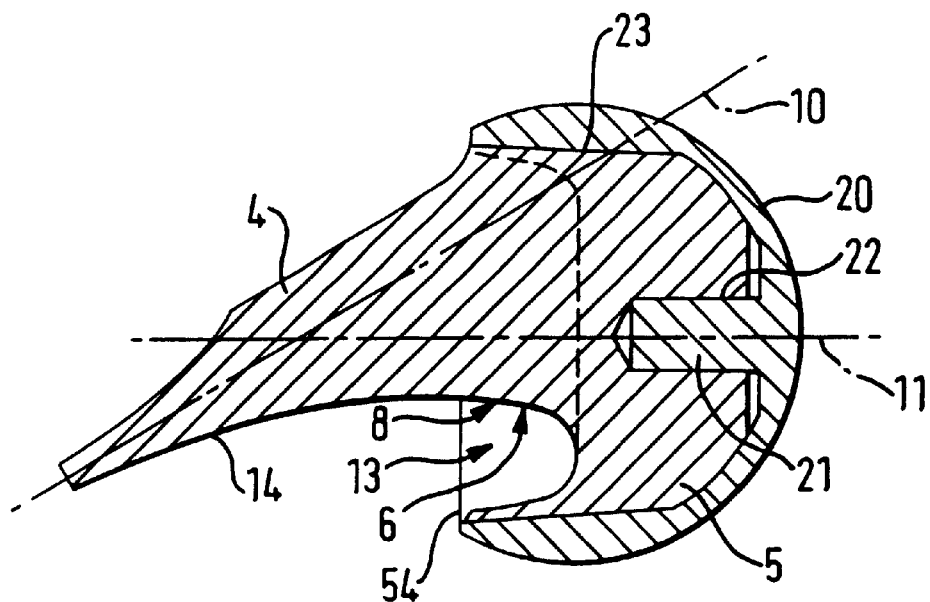
FIG. 3 is a cross-sectional side elevation of the construction shown in FIG. 2 but of a multiple construction.

The general axis of the tapered insert portion 4 is indicated by reference numeral 10 in FIGS. 3 and 4 and is inclined to the general axis 11 of the head portion 5 in a plane radial to the axis 10. The general axis 11 is substantially aligned with the distal-proximal axis 9 of the neck 2 when the component is in position.

Figure 2:
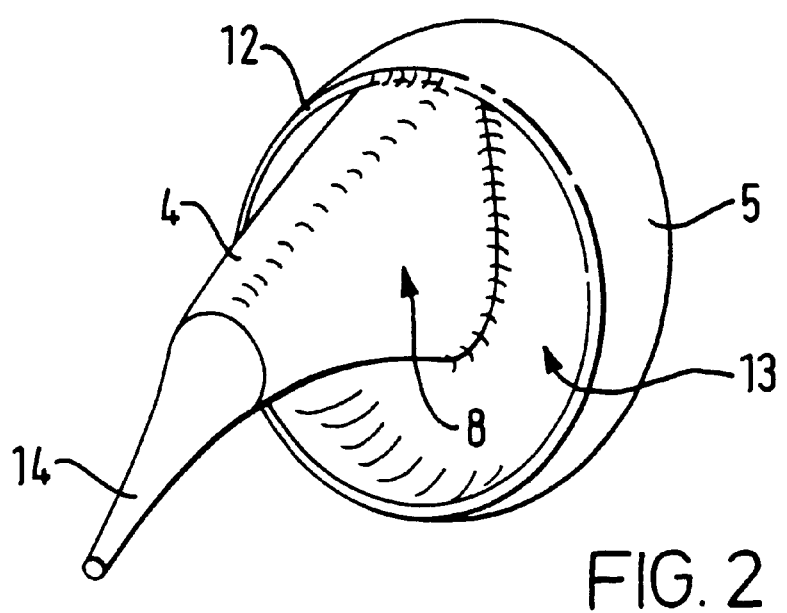
FIG. 2 is an isometric view of a prosthetic femoral component according to the invention and which is formed as a single metal component.

FIG. 2 shows that in the preferred embodiment, the tapered insert portion is of non-circular cross-section and is shaped to prevent rotation relative to the bone. Thus, the cross-section of this insert portion 4 is generally elongate in a medial and lateral plane extending normal to the central axis 11 of the head 5 and in this construction is substantially rectangular in cross-section.

The preferred insert portion 4 extends radially away from the distal rim 12 of the head portion 5 towards the central axis 11 and the distal side of the head portion 5 is formed as a trough 13 where it surrounds the tapered insert portion. The distal portion 14 of the preferred insert portion 4 is formed as a regular or irregular concave taper 15.

The insert portion 4 extends radially away from the distal rim 12 of the head portion 5 towards the central axis 11 and the distal side of the head portion 5 is formed as a trough 13 where it surrounds the tapered insert portion 4.

The distal portion 14 of the insert portion 4 is formed as a regular or irregular concave taper 15.

FIG. 2 shows a construction which is made from metal or a synthetic plastics material or a ceramic material and is formed as a single component.

FIGS. 3 to 6 show alternative embodiments similar to that shown in FIG. 2 but of multiple construction.

In the arrangement shown in FIG. 3 a substantially part-spherical bearing element 20 is provided and the proximal end of the head portion 5 is provided with a male taper 23 to receive a matching female taper on the part-spherical bearing element 20. This bearing element 20 has a spigot or trunnion 21 which is provided with a Morse taper adapted to engage in a co-operating Morse tapered bore 22 provided in the head portion 5. This provides and engaging fit. Alternatively, the spigot 21 and the bore 22 could be cylindrical.

In the construction shown in FIG. 4 however the bearing element 20 has an elongated Morse tapered spigot or trunnion 25 which extends through the head portion 5 and into the tapered insert portion 4 in an extended Morse tapered bore 22. In the construction shown the proximal end of the head portion 5 is substantially hemispherical as is the inner wall 26 of the bearing element 20.

In these constructions the tapered insert portion may conveniently be made of a synthetic plastic material and the bearing element 20 of any other suitable material, for example metal. If desired however both the tapered insert portion and the outer bearing element 20 can be made of the same material. Again the tapered insert portion 4 and head portion 5 can be made from a ceramic material, for example alumina, zirconium or zirconium toughened alumina.

FIG. 4 indicates how the bone is cut to receive this type of prosthetic femoral component. The natural head of the femur is resectioned immediately above the neck 2 and is cut to provide a bore on the axis 11. A second bore is then cut at an angle to the first on the line of the axis 10. The opening provided by the bores is enlarged and tapered outwardly to provide a tapering opening which is substantially rectangular in cross-section.

To carry out this procedure the preparation is as follows:

Step 1: the femoral head is cut around the equator using an oscillating saw.

Step 2: a guide rod is placed along the axis of the femoral neck.

Step 3: nibblers are used to clean around the femoral head to create a cylindrical shape.

Step 4: an external conical reamer is used to ream the head to correct height and prepare the contact surface for the prosthesis using a trial cap to gauge the approximate depth of cut.

Step 5: the trial cap is used to protect the femoral head while the acetabulum is prepared.

Step 6: when the acetabulum is in place a trial reduction is performed with the trial cap and the trial head to ensure that the femur has been prepared to correct height before completing preparation of the internal cavity in the femur.

Step 7: the trial head is removed and the two bores are reamed in the bone through the trial cap which can also act as a reaming guide. The shape of the reamer gives the flared shape to the bone at least on the medial side.

Step 8: the trial cap is remove and the cavity is finished with either an osteotom or a rasp.

The prosthesis is now fitted as described above.

If desired the proximal end of the cut opening can be cut to provide a series of radially inwardly extending steps or fins (not shown). Such steps or fins are described in our co-pending application filed on the same date as this application claiming priority of U.K. 0007392.4. Similar steps, or fins, (again not shown) can be provided on the flared part of the insert portion to encourage growth of the trabeculum fibers to reform around the sharp corners of the steps or fins.

The particular shape of the stem shown in FIGS. 3, 4 and 5 prevents rotation of the stem in the bone and makes it easy to implant with enhanced stability. The advantage of the invention is that it involves minimally invasive surgery.

The insert portion 4 and the head portion 5 can be made of any suitable materials, for example in the preferred embodiment a synthetic resin and carbon fibers, typical example being PEEK (polyetheretherketone) or PBT (polybutalieneterephthalate) resin into which a chopped carbon fiber can be incorporated. Preferably the material is of a similar compressive modulus as cancellous bone. In all the above constructions the surface finish of parts which abut bone can be in the form of a cut-away honeycomb.

The insert portion and proximal head portion can be made from any of the materials referred to above and be coated with plasma sprayed hydroxyapatite (HA) which is osteoconductive and stimulates bone growth. If desired it could be made from metal, for example, titanium, with a porous coating.

In the constructions described above the stem is driven into the bone but it could be held by cement. Thus a small amount of cement could be applied at the proximal end of the stem, bone growth being relied upon towards the distal end.

In the construction described above the tapered insert portion extends through the neck 2 of the femur but if desired the arrangement could be such that it is only of short length and does not pass through the neck portion.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A femoral hip implant for implantation in the head-neck region of the femur head comprising:
a head portion having an insert portion for insertion within the neck region of the femur, said head portion having a distal rim portion contacting an outer surface of the femur with the insert portion extending from adjacent the rim portion radially away from the rim portion towards a central distal-proximal axis of the neck of the femur and having a distally facing cup-shaped surface flaring outwardly in the medial direction from an outer surface of said insert portion, said distal surface extends in a direction perpendicular to the central distal-proximal axis of the neck a distance greater than the minimum dimension of the neck in a plane perpendicular to said axis.

2. The femoral implant as set forth in claim 1 further comprising a part-spherical bearing element mounted on a proximal outer surface of said head portion.

3. The femoral implant as set forth in claim 2 wherein the bearing element has a tapered trunnion extending distally from an inner surface of the bearing element and said head portion has a complimentary tapered bore formed therein.

4. The femoral implant as set forth in claim 1 wherein said cup-shaped flared surface includes a proximal portion extending from said insert portion and a distally extending portion spaced medially from said proximal portion and connected thereto by a distally facing concave surface.

5. The femoral implant as set forth in claim 4 wherein said cup-shaped flared surface extends about said neck axis anteriorly and posteriorly from said medial flared surface to said insert portion on said lateral side of said rim portion.

6. The femoral implant as set forth in claim 5 wherein said cup-shaped flared surface includes a proximal portion extending from said insert portion and a distally extending portion spaced medially from said proximal portion and connected thereto by a distally facing concave surface.

7. The femoral implant as set forth in claim 4 wherein said insert portion has an inwardly tapered outer surface extending distally from said cup-shaped flared surface.

8. The femoral implant as set forth in claim 7 wherein said tapered surface is inclined with respect to the neck central axis in the direction of a longitudinal proximal-distal axis of the femur.

9. The femoral implant as set forth in claim 7 wherein said insert has a proximal portion having a non-circular cross-section.

10. The femoral implant as set forth in claim 9 wherein said tapered insert portion has a distal portion formed as a regular or irregular concave taper.

11. The femoral implant as set forth in claim 2 wherein said proximal outer surface of said head portion is tapered and said bearing element has an inner tapered surface complimentary to said tapered outer surface on said head portion for mating with said head portion.

12. The femoral implant as set forth in claim 11 wherein said tapered surfaces are Morse locking tapers.

13. The femoral hip implant as set forth in claim 1, wherein said insert has a portion which extends towards said neck central axis from adjacent the lateral side of said rim portion.

14. A prosthetic femoral component for location in a prepared socket in a femur which has been resected at a position on the proximal side of its neck said component comprising a tapered insert portion and a proximal head portion having a distal rim portion contacting the femur with the insert portion extending from adjacent the rim radially away from the rim portion towards a central distal-proximal axis of the neck of the femur and a proximal end of said insert portion being adapted for location in said prepared socket and having a maximum dimension in a plane normal to the distal-proximal central axis of the neck which is larger than the minimum dimension of the neck in a parallel plane.

15. The prosthetic femoral component as claimed in claim 14 in which said tapered insert portion is flared outwardly in a proximal direction.

16. The prosthetic femoral component as claimed in claim 14 in which said tapered insert portion is dimensioned to pass through the neck of the femur with which it is to be used.

17. The prosthetic femoral component as claimed in claim 14 in which the tapered insertion portion has a smooth finish.

18. The prosthetic femoral component as claimed in claim 14 in which a proximal end of the head portion is of a generally spherical shape and has a bearing surface for co-operation with an acetabular socket.

19. The prosthetic femoral component as claimed in claim 18 in which the bearing element is made from a ceramic material.

20. The prosthetic femoral component as claimed in claim 19 in which the ceramic material is alumina, zirconium or zirconium toughened alumina.

21. The prosthetic femoral component as claimed in claim 14 in which the proximal end of the head portion is adapted to receive a substantially part-spherical bearing element.

22. The prosthetic femoral component as claimed in claim 21 in which an outer surface on the proximal end of the head portion is provided with a male taper to receive a matching female tapered inner surface on the part-spherical bearing element.

23. The prosthetic femoral component as claimed in claim 20 in which the bearing element has a spigot adapted to engage in a bore provided in the insert portion of the head portion.

24. The prosthetic femoral component as claimed in claim 23 in which the spigot and bore are tapered to provide an engaging fit.

25. The prosthetic femoral component as claimed in claim 24 in which the spigot is elongated and extends through an opening in the head portion and into the bore in the insert portion.

26. The prosthetic femoral component as claimed in claim 19 in which the head portion has an outer surface at a proximal end thereof which is substantially hemispherical, the bearing element having a complimentary inner wall which is substantially hemispherical and which has a tapered elongate spigot adapted to engage in a tapered bore in the head portion to provide an engaging fit and the spigot extends through a bore in the head portion and into the tapered insert portion.

27. The prosthetic femoral component as claimed in claim 14 in which the tapered insert portion is made of metal.

28. The prosthetic femoral component as claimed in claim 14 in which the tapered insert portion is made of a synthetic plastics material.

29. The prosthetic femoral component as claimed in claim 28 in which the tapered insert portion and head portion are made from a synthetic resin and carbon fibres.

30. The prosthetic femoral component as claimed in claim 29 in which the synthetic resin is PEEK (polyetheretherketone) or PBT (polybutalieneterephthalate) into which chopped carbon fibre is incorporated.

31. The prosthetic femoral component as claimed in claim 30 in which the material is of a similar compressive modulus to cancellous bone.

32. The prosthetic femoral component as claimed in claim 31 in which the surface finish of parts which abut bone are in the form of a cut-away honeycomb.

33. The prosthetic femoral component as claimed in claim 14 in which the tapered insert portion and head portion are made from a ceramic material.

34. The prosthetic femoral component as claimed in claim 33 in which the ceramic material is alumina, zirconium or zirconium toughened alumina.

35. The prosthetic femoral component as claimed in claim 14 in which the portions of the component which contact bone are coated with plasma sprayed hydroxyapatite (HA).

36. The prosthetic femoral component as claimed in claim 35 in which the insert portion is adapted to be driven into the bone and held without cement.

37. The prosthetic femoral component as claimed in claim 14 in which the insert portion is adapted to be held by cement at the proximal end of the insert portion.

38. The prosthetic femoral component as claimed in claim 14 which is formed as a single component.

39. The prosthetic femoral component as claimed in claim 14 in which tapered insert portion has a central axis which is inclined to the neck central axis in a plane radial thereto.

40. The prosthetic femoral component as claimed in claim 14 in which the tapered insert portion is non-circular and is adapted to prevent rotation relative to the bone.

41. The prosthetic femoral component as claimed in claim 40 in which the cross-section of the tapered insert portion is elongate in a plane extending normal to the insert central axis.

42. The prosthetic femoral component as claimed in claim 41 in which the cross-section of the tapered insert portion is substantially rectangular, oval, or figure-of-eight shaped.

43. The prosthetic femoral component as claimed in claim 14 in which a distal side of the head portion is formed as a trough which extends around part of the tapered insert portion.

44. The prosthetic femoral component as claimed in claim 14 in which a distal portion of the tapered insert portion is formed with a rectangular or irregular concave taper.

45. The prosthetic femoral component as claimed in claim 14 in which the proximal end of the tapered insert portion is provided with a series of radially outwardly extending steps or fins.

46. A method for implanting a femoral hip prosthesis on the head and neck of the femur comprising:
    resecting the femoral head around an equatorial plane thereof;
    forming a pair of bores in the femoral head a first bore of said pair inclined relative to a central axis of the neck;
    forming a flared external portion on the medial side of the head; and
    placing a prosthetic femoral component having a tapered insert portion and a proximal head portion having a distal rim portion contacting an outer surface of the resected head of the femur with the insert portion extending from adjacent the rim portion radially away from the rim portion towards a central distal-proximal axis of the neck of the femur and a proximal end of said insert portion being adapted for location in a second of said prepared pair of bores and said tapered insert portion extending into said first bore and said proximal end of said insert portion having a maximum dimension in a plane normal to the distal-proximal central axis of the neck which is larger than the minimum dimension of the neck in a parallel plane.

47. The method for implanting a femoral hip prosthesis as set forth in claim 46 further comprising forming a series of radially extending steps increasing in diameter on moving proximal to distal on the resected head of the femur.

48. The method for implanting a femoral hip prosthesis as set forth in claim 47 wherein the femoral component has complimentary surfaces which engage said steps.

49. The method for implanting a femoral hip prosthesis as set forth in claim 46, wherein said second bore extends towards said neck central axis from adjacent a lateral side of said femoral head.

50. A femoral implant for implantation in the head-neck region of the femur head comprising:

a bearing element having a generally hemispherical outer surface and a conically tapered female inner surface; and a head portion having an insert portion for insertion within the neck of the femur, said head portion having a distally facing cup-shaped surface flaring outwardly in the medial direction from an outer surface of said insert portion, said distal surface extends in a direction perpendicular to a central distal-proximal axis of the neck a distance greater than the minimum dimension of the neck in a plane perpendicular to said axis, said head portion having a conically tapered male outer surface for mating with said tapered inner surface of said bearing element.

51. The femoral implant as set forth in claim 50, wherein the bearing element includes a trunnion extending distally from the inner surface thereof and said head portion having a complimentary bore therein for receiving the trunnion.

* * * * *

UNITED STATES PATENT AND TRADEMARK OFFICE
CERTIFICATE OF CORRECTION

PATENT NO. : 6,524,343 B2
DATED : February 25, 2003
INVENTOR(S) : John Andrew Storer, Richard Eddy Field and Neil Rushton It is certified that error appears in the above-identified patent and that said Letters Patent is hereby corrected as shown below:

<u>Title page,</u>
Item [75], "Walton-on-the-Hill" should read -- Surrey --.
Item [57], ABSTRACT,
Line 3, "Includes" should read -- includes --.

<u>Column 2,</u>
Line 13, "Gerard" (first occurrence) should read -- Gérard --.
Line 13, "(Gerard)" (second occurrence) should read -- (Gérard) --.

<u>Column 3,</u>
Line 16, cancel ",".

<u>Column 9,</u>
Line 16, "20" should read -- 22 --.
Line 28, "19" should read -- 21 --.

Signed and Sealed this

Twelfth Day of August, 2003

JAMES E. ROGAN
*Director of the United States Patent and Trademark Office*